United States Patent [19]

Van Rompuy et al.

[11] Patent Number: 5,348,836
[45] Date of Patent: Sep. 20, 1994

[54] SILVER HALIDE PHOTOGRAPHIC MATERIAL

[75] Inventors: Ludo Van Rompuy, Destelbergen; Jean-Marie Dewanckele, Drongen, both of Belgium

[73] Assignee: AGFA-Gevaert, N.V., Mortsel, Belgium

[21] Appl. No.: 50,672

[22] Filed: Apr. 22, 1993

[30] Foreign Application Priority Data

May 13, 1992 [EP] European Pat. Off. ........ 92201365.1

[51] Int. Cl.$^5$ ........................... G03C 5/54; G03C 1/06
[52] U.S. Cl. ..................................... 430/204; 430/230; 430/202; 430/244; 430/251; 430/445; 430/446; 430/448; 430/234; 430/509; 430/598; 430/599; 430/600; 430/603; 430/955
[58] Field of Search ............... 430/204, 230, 251, 509, 430/234, 598, 599, 955, 617, 603, 244, 600, 445, 446, 448, 202

[56] References Cited

U.S. PATENT DOCUMENTS

| | | | |
|---|---|---|---|
| 4,518,682 | 5/1985 | Kobayashi et al. | 430/598 |
| 4,526,863 | 7/1985 | Mihayashi et al. | 430/598 |
| 4,693,955 | 9/1987 | Torizuka et al. | 430/230 |
| 4,724,199 | 2/1988 | Kobayashi et al. | 430/598 |
| 4,772,535 | 9/1988 | Yamano et al. | 430/230 |
| 5,068,165 | 11/1991 | Coppens et al. | 430/230 |

*Primary Examiner*—Richard L. Schilling
*Attorney, Agent, or Firm*—Breiner & Breiner

[57] ABSTRACT

The present invention provides a photographic material comprising on a support photosensitive silver halide particles, and substantially light insensitive silver salt particles having a speed at least a factor 10 less under the same conditions of exposure and development of said photosensitive silver halide particles than said photosensitive silver halide particles and a releasing compound of formula (I) or (II) as specified in the claims capable of image-wise releasing sulphide or a sulphide under conditions for image-wise development of said photosensitive silver halide particles to silver. The present invention further provides a method for obtaining an image and a lithographic printing plate with said photographic material.

32 Claims, No Drawings

SILVER HALIDE PHOTOGRAPHIC MATERIAL

FIELD OF THE INVENTION

The present invention relates to a photographic material and a method for producing images therewith.

BACKGROUND OF THE INVENTION

In the art of silver halide photography it is well known to use compounds that image-wise release a photographic useful group such as e.g. a dye or dye precursor, a silver halide solvent, a fogging agent, an anti-fogging agent, a development inhibitor, a development accelerator, a developing agent, a chemical or spectral sensitizing agent, a toning agent etc.. Some of these type of compounds are commonly employed to produce colour images (see for example Angew. Chem. Int. Ed. Engl. 22 pages 191–209, 1983) but are also useful in black and white materials to obtain a photographic material having a high speed, high contrast etc.. For example U.S. Pat. No. 4,724,199 discloses compounds capable of releasing a fogging agent to obtain a photographic material of high speed and high contrast.

Some of these type of compounds may also be used to obtain a negative working silver salt diffusion transfer material. See for example U.S. Pat. No. 4,693,955 and the Japanese published unexamined patent application no. 15247/59. By the term "negative working" is meant that the exposed parts of the photographic material yield the image parts while the term "positive working" implies the formation of image parts corresponding to the non-exposed parts of the photographic material.

SUMMARY OF THE INVENTION

It is an object of the present invention to provide a negative or positive working photographic material of high speed.

It is a further object of the present invention to provide a method for obtaining an image of high contrast, high sharpness and high resolution with said photographic material.

It is a third object of the present invention to provide a method for making a negative or positive working lithographic printing plate based on the silver salt diffusion transfer process using said photographic material.

Further objects will become clear from the description hereinafter.

According to the present invention there is provided a photographic material comprising on a support photosensitive silver halide particles, and substantially light insensitive silver salt particles having a speed at least a factor 10 less under the same conditions of exposure and development of said photosensitive silver halide particles than said photosensitive silver halide particles and a releasing compound of formula (I) or (II) capable of image-wise releasing sulphide or a sulphide under conditions for image-wise development of said photosensitive silver halide particles to silver:

$$\text{CARRIER}-(\text{TIME})_n-\text{S}-\text{A} \quad (I)$$

$$(II)$$

CARRIERS wherein CARRIER represents a carrier moiety that upon reaction with either the reduced or oxidized form of a developing agent or upon reaction with silver ions is capable of releasing under the conditions of development of said photosensitive silver halide the moiety $-(\text{TIME})_n-\text{S}-\text{A}$, $-\text{S}-\text{A}$ or sulphide, TIME represents a so called timing group which releases $-\text{S}-\text{A}$ or sulphide subsequent to the release of $-(\text{TIME})_n-\text{S}-\text{A}$ from CARRIER, A represents an organic group that renders the bond between S and A readily splittable under the development conditions of said photosensitive silver halide and n represents 0 or 1.

According to the present invention there is also provided a method for making an image using the photographic material defined above.

According to the present invention there is also provided a method for making a negative or positive working lithographic printing plate using the photographic material defined above.

DETAILED DESCRIPTION OF THE INVENTION

In the method of the present invention during the development step sulphide rendering the substantially light insensitive silver salt particles developable is released either mainly in the exposed or mainly in the non-exposed areas. Sulphide can be directly released from the carrier moiety in absence of a timing group and the instance that the group A is split off before -S-A is released from the carrier moiety. In all the other cases a sulphide will first be released from the carrier moiety which then releases sulphide ($S^{2-}$).

According to a first embodiment of the present invention compounds that preferably release sulphide in their reduced state can be incorporated in the photographic material in their reduced state. Thus for a negative working photosensitive silver halide emulsion during development the developing agent will be oxidized in the exposed areas and will be able to oxidize the releasing compound in the exposed areas. In the non-exposed areas the developing agent will remain in its reduced state thus not being able to oxidize the releasing compound. Since the reduced form of the releasing compound according to this first embodiment preferably releases sulphide under the conditions of development of the photosensitive silver halide sulphide will be mainly released in the non-exposed areas thus rendering the substantially light insensitive silver salt particles developable in the non-exposed areas. Therefore in the exposed areas only the photosensitive silver halide will be developed while in the non-exposed areas the substantially light insensitive silver salt particles will be developed and probably also the photosensitive silver halide. Since the combination of the photosensitive silver halide and substantially light insensitive silver salt can be choosen such that mainly the substantially light insensitive silver salt contributes to building up of density e.g. by using more light insensitive silver salt than photosensitive silver halide or by using a coarse grain photosensitive silver halide and a fine grain light insensitive silver salt the density in the exposed parts will be less than in the non-exposed parts.

According to a second embodiment the releasing compound can be incorporated in its oxidized state and mainly the reduced form of the releasing compound is capable of releasing sulphide. During development of a negative working photosensitive silver halide emulsion the developing agent will be consumed in the exposed areas due to development of the exposed silver halide and as a consequence the releasing compound mainly remains in its oxidized state in the exposed areas. In the non-exposed areas the releasing compound will be reduced by the developing agent so that the release of sulphide in the non-exposed areas will be enabled under the conditions of development. As a consequence sulphide will be mainly released in the non-exposed areas where it renders the substantially light insensitive silver salt particles developable. Similar as explained in the first embodiment this will result in a larger density in the non-exposed parts than in the exposed parts.

According to a third embodiment of the present invention a releasing compound capable of preferably releasing in its oxidized form sulphide is incorporated in the oxidized state. During development the developing agent will be consumed in the exposed areas of a negative working photosensitive silver halide emulsion due to development of the exposed silver halide so that the releasing compound remains in the oxidized state in the exposed areas and will be reduced in the non-exposed areas by the developing agent. As a consequence sulphide will be mainly released in the exposed areas where it will render the light insensitive silver salt particles developable. In this embodiment none or pratically none of the silver halide and silver salt in the non-exposed areas will be developed while both the photosensitive silver halide and substantially light insensitive silver salt in the exposed areas will be developed. This embodiment and the subsequent fourth and fifth embodiment that operate in a similar way offer the advantage over a silver halide material containing no releasing compound and substantially light insensitive silver salt that high speed photosensitive materials can be obtained without loss of image quality especially the image density.

According to a fourth embodiment of the present invention a releasing compound capable of preferably releasing in its oxidized form sulphide is incorporated in the reduced state. During development the developing agent will be oxidized in the exposed areas of a negative working photosensitive silver halide emulsion due to development of the exposed silver halide so that the oxidized form of the developing agent will be capable of oxidizing the releasing compound to its oxidized state in these areas while the releasing compound will remain in its reduced state in the non-exposed areas. As a consequence sulphide will be mainly released in the exposed areas where it will render the light insensitive silver salt particles developable.

According to a fifth embodiment of the present invention releasing compounds can be used that release sulphide upon a coupling reaction with the oxidized form of the developing agent. During development the developing agent will be oxidized in the exposed parts of a negative working photosensitive silver halide emulsion so that in these areas a coupling reaction of the oxidized form of a developing agent with the releasing compound to release sulphide can take place. As a consequence the substantially light insensitive silver salt particles will be rendered developable in the exposed parts of the photographic material.

According to a sixth embodiment of the present invention a releasing compound can be used that releases sulphide under the developing conditions upon reaction with silver ions. Since the silver ions are developed to silver in the exposed parts of a negative working photosensitive silver halide emulsion the reaction will mainly take place in the non-exposed areas of the photosensitive silver halide emulsion so that sulphide will be released in the non-exposed areas.

Depending upon the type of releasing compound and the releasing mechanism it is thus possible to manufacture a negative or positive working photographic material comprising a negative working photosensitive silver halide emulsion. It is further clear to a person skilled in the art that when a positive working photosensitive silver halide emulsion is used the release of sulphide will take place in areas opposite in image value with regard to the areas where release takes place in the negative working emulsions.

Preferred releasing compounds for use in accordance with the present invention correspond to general formula (III) to (VI) or the oxidized form thereof:

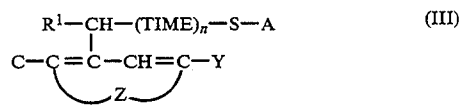

(III)

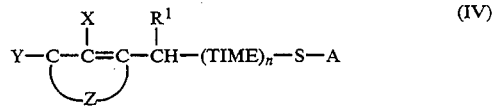

(IV)

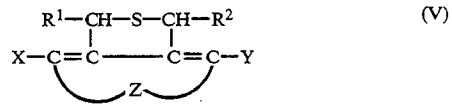

(V)

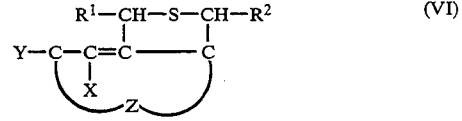

(VI)

wherein $R^1$, $R^2$ each independently represents hydrogen or an alkyl containing 1 to 5 carbon atoms;

Z represents the necessary atoms for completing an aromatic ring including heterocyclic rings and fused ring systems preferably a benzene or napthalene ring and that may be substituted with one or more substituents e.g. an alkyl, aryl, alkylaryl, aralkyl alkoxy, aryloxy or alkoxyaryl each of which may be substituted, $-SO_2-R^O$ with $R^O$ an alkyl, aryl, aralkyl or alkylaryl each of which may be substituted, $-CR^1-S-A$ etc.;

X represents $-OR^3$ with $R^3$ hydrogen or a hydrolizable group yielding hydroxy, $-NHR^4$ with $R^4$ an alkyl, aryl, aralkyl each of which may be substituted, $-N=O$ or $-NO_2$;

Y represents independently from X represents one of the significances given for X or $-NHSO_2-R^4$;

and A, TIME and n are as defined above.

Preferred organic groups A that render the bond between S and A readily splittable are e.g. hydrogen, acyl, para-hydroxy benzyl, ortho-hydroxy benzyl each of which may be substituted, $-CH_2-NHCOR$, $-CH_2-O-COR$ with R a hydrogen, alkyl, aryl or aralkyl each of which may be substituted.

By the term "readily splittable" is meant that for a substantial amount of the releasing compound the bond between S and A is splitted or broken during the development of the photographic material so that a substantial amount of sulphide is released thereby rendering the substantially light insensitive silver halide particles developable to obtain the effect of the present invention.

Examples of releasing compounds suitable for use in accordance with the present invention are:
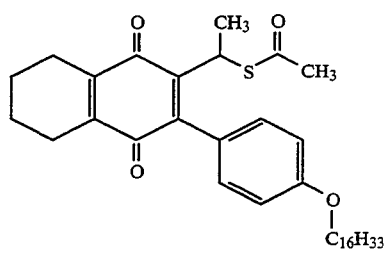
1
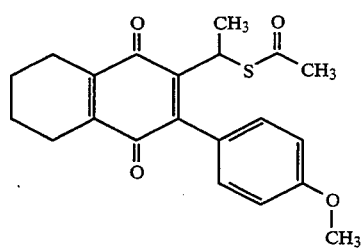
2
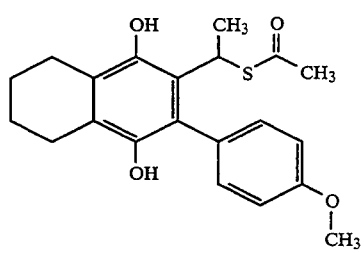
3
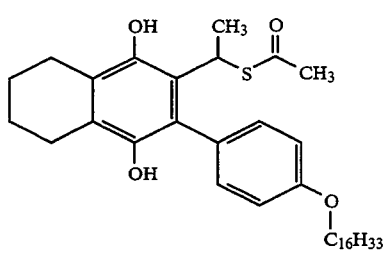
4
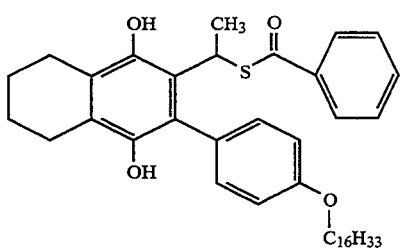
5
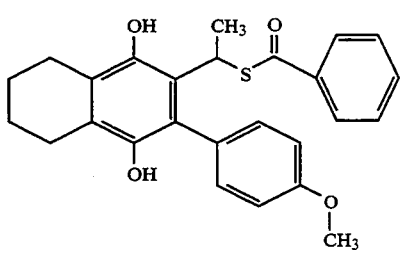
6
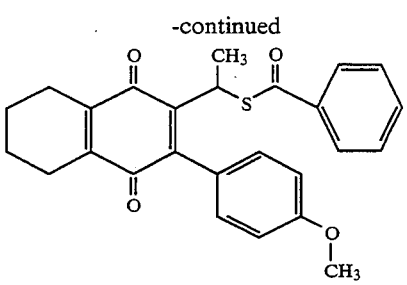
7
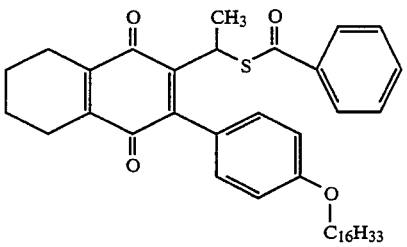
8
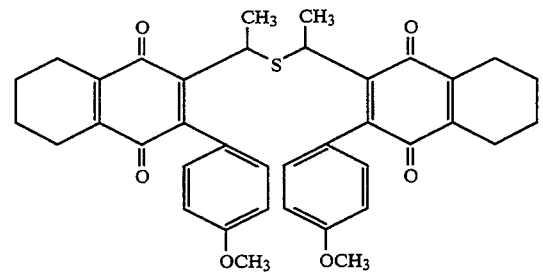
9
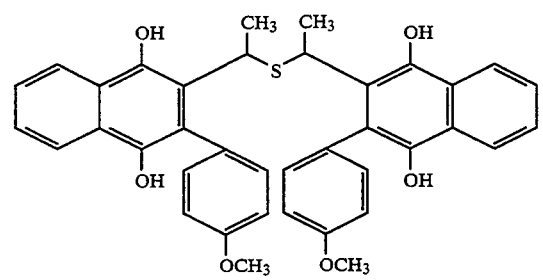
10
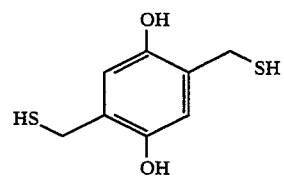
11
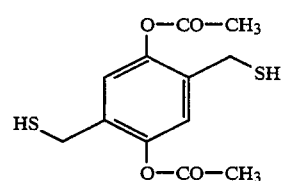
12
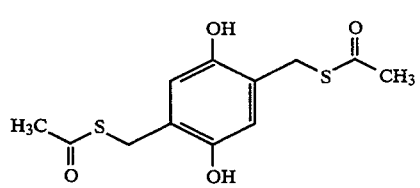
13

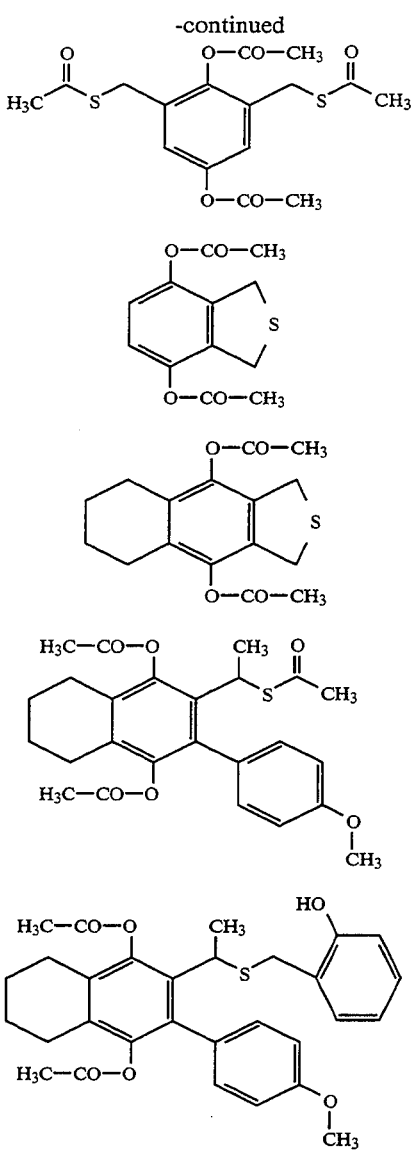

The above mentioned compounds can be prepared according to known procedures. For example products 1 to 8 and 17 can be prepared by reacting the appropriate 2-chloroethyl substituted chinon derivative with the appropriate mercaptoacetyl compound. This procedure is exemplified for compound 1 (see below). Compounds 11 to 16 can be prepared as described in J. Org. Chem., 30, (1965) pages 247 to 249.

Preparation of compound 1

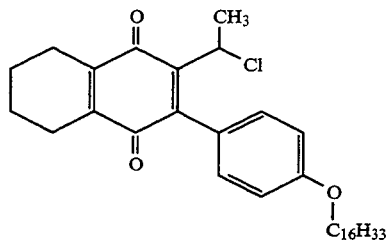

compound A

To a solution of 0.8 g of sodium hydroxide in 22.5 ml of methanol was dropwise added under a nitrogen atmosphere 1.5 g of thiolacetic acid whilst stirring. To this mixture was then added 22.5 ml of a tetrahydrofuran solution of the above show compound A whilst stirring (compound A can be prepared as described in EP.A 0 527 521). After completion of the exothermic reaction the mixture was cooled to room temperature and the obtained precipitate was separated, washed with methanol and subsequently dried. A yield of 77% of compound 1 was obtained. The melting point was 84° C.

The sulphide releasing compounds used in accordance with the present invention may be present in one or more layers on the side of the support carrying the photosensitive silver halide. Preferably the sulphide releasing compound is present in the layer containing the photosensitive silver halide. The amount of sulphide releasing compound(s) comprised in the photographic material may be varied widely but is preferably between 0.1 mmol/m² and material may be varied widely but is preferably between 0.1 mmol/m² and 1 mmol/m².

The photosensitive and substantially light insensitive silver salt particles used in accordance with the present invention may be present in one or in separate layers. When they are present in separate layers the order of both layers may be varied as desired with respect to the support and intermediate water permeable layers of e.g. gelatin may be provided. Preferably the photosensitive and substantially light insensitive silver salt are present in the same layer.

To take most advantage of the present invention it is important that the substantially light insensitive silver salt particles have a speed at least a factor 10 preferably a factor 100 less than the photosensitive silver halide used under the same conditions of development and exposure of the photosensitive silver halide. If the difference in speed is less than a factor 10 the substantially light insensitive silver salts will be rendered developable by the exposure of the imaging element which should be avoided as much as possible to take most advantage of the present invention.

Preferred substantially light insensitive silver salts used in accordance with the present invention are water insoluble silver salts e.g. a silver halide, bromate, molybdate, oxalate, chromate, iodate, isocyanate, thioisocyanate, cyanide, citrate, phosphate, oxide etc. Said substantially light insensitive water insoluble silver salts may be prepared using the precipitation reaction of the water soluble salt of the desired anion of the insoluble silver salt with a water soluble silver salt, e.g. silver nitrate, in the presence of a hydrophilic binder. Silver halides containing at least 70 mol % of chloride are preferred in the present invention for use as the substantially light insensitive silver salt particles.

As already mentioned above the substantially light insensitive silver halide particles are preferably fine particles i.e. having a diameter of less than 0.5 μm. The silver halide is preferably also doped with $Rh^{3+}$, $Ir^{4+}$, $Cd^{2+}$, $Zn^{2+}$ and/or $Pb^{2+}$ to reduce the light sensitivity of the silver salt. The silver halide preferably is not chemically sensitized nor spectrally sensitized i.e. a so called primitive silver halide emulsion. The silver salt particles may further be desensitized on the surface with a desensitizing agent well known to those skilled in the art. Examples of desensitizing agents are disclosed in e.g. the U.S. Pat. Nos. 2,930,644, 3,431,111, 3,492,123, 3,501,310, 3,501,311, 3,574,629, 3,579,345, 3,598,595, 3,592,653, 4,820,625, 3,933,498, and GB 1,192,384. Further desensitizing agents suitable for use in accordance with the present invention are described e.g. by P. Glafkides in "Chimie et Physique Photographique", Paul Montel, Paris (1967). Agents that retard the dissolution of silver salt particles by a silver halide solvent may also be added. For example 5-nitro-indazole, ballasted mercapto-heterocyclic compounds etc. can be used for this purpose.

The photosensitive silver halide emulsion can be prepared from soluble silver salts and soluble halides according to different methods as described e.g. by P. Glafkides in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966).

The photosensitive silver halide emulsion used according to the present invention can be prepared by mixing the halide and silver solutions in partially or fully controlled conditions of temperature, concentrations, sequence of addition, and rates of addition. The silver halide can be precipitated according to the single-jet method or the double-jet method.

The photosensitive silver halide particles of the photographic material used according to the present invention may have a regular crystalline form such as a cubic or octahedral form or they may have a transition form. They may also have an irregular crystalline form such as a spherical form or a tabular form, or may otherwise have a composite crystal form comprising a mixture of said regular and irregular crystalline forms.

According to the present invention the photosensitive silver halide emulsion preferably consists principally of silver chloride while a fraction of silver bromide is present ranging from 1 mole % to 40 mole %. However other silver halide compositions can also be used in accordance with the present invention. The silver halide may be of the core/shell type well known to those skilled in the art in the sense that substantially all the bromide is concentrated in the core. This core contains preferably 10 to 40% of the total silver halide precipitated, while the shell consists preferably of 60 to 90% of the total silver halide precipitated.

The average size of the photosensitive silver halide grains may be varied widely but preferably is between 0.2 and 5 $\mu$m, most preferably between 0.3 and 2 $\mu$m. The photosensitive silver halide particles are preferably of high speed. It is furthermore advantageous that the photosensitive silver halide particles show a rapid chemical development i.e. silver halide emulsions that show a complete chemical development within at least 15s. The rate of chemical development can be easily determined with the following method. The silver halide emulsion layer of which the rate of chemical development is to be measured is coated to a transparent support in an amount equivalent to 2 g of AgNO/m3/m² and 2.1 g of gelatin/m². The thus obtained element is exposed to a suitable light-source and subsequently placed in a cuvette in a spectrophotometer and thermostated at 25° C. A developing solution is brought in the cuvette and the absorption at 800 nm is followed with time. From the plot of the absorption at 800 nm against time the time necessary to obtain a complete development of the sample can be determined.

The size distribution of the silver halide particles of the photosensitive silver halide particles to be used according to the present invention can be homodisperse or heterodisperse. A homodisperse size distribution is obtained when 95% of the grains have a size that does not deviate more than 30% from the average grain size.

Preferably during the precipitation stage Iridium and/or Rhodium containing compounds or a mixture of both are added. The concentration of these added compounds ranges from $10^{-8}$ to $10^{-3}$ mole per mole of AgNO$_3$, preferably between $10^{-7}$ and $10^{-4}$ mole per mole of AgNO$_3$. This results in the building in the silver halide crystal lattice of minor amounts of Iridium and/or Rhodium, so-called Iridium and/or Rhodium dopants. As known to those skilled in the art numerous scientific and patent publications disclose the addition of Iridium or Rhodium containing compounds or compounds containing other elements of Group VIII of the Periodic System during emulsion preparation.

The photosensitive silver halide emulsion can be chemically sensitized e.g. by adding sulphur-containing compounds during the chemical ripening stage e.g. allyl isothiocyanate, allyl thiourea, and sodium thiosulphate. Also reducing agents e.g. the tin compounds described in BE-P 493,464 and 568,687, and polyamines such as diethylene triamine or derivatives of aminomethane-sulphonic acid can be used as chemical sensitizers. Other suitable chemical sensitizers are noble metals and noble metal compounds such as gold, platinum, palladium, iridium, ruthenium and rhodium. This method of chemical sensitization has been described in the article of R. KOSLOWSKY, Z. Wiss. Photogr. Photophys. Photochem. 46, 65–72 (1951).

The photosensitive silver halide emulsion of the photographic element of the present invention can be spectrally sensitized according to the spectral emission of the exposure source for which the photographic element is designed.

Suitable sensitizing dyes for the visible spectral region include methine dyes such as those described by F. M. Hamer in "The Cyanine Dyes and Related Compounds", 1964, John Wiley & Sons. Dyes that can be used for this purpose include cyanine dyes, merocyanine dyes, complex cyanine dyes, complex merocyanine dyes, holopolar cyanine dyes, hemicyanine dyes, styryl dyes and hemioxonol dyes. Particularly valuable dyes are those belonging to the cyanine dyes, merocyanine dyes, complex merocyanine dyes.

In case of exposure by a semiconductor laser special spectral infra-red sensitizing dyes are disclosed in i.a. U.S. Pat. Nos. 2,095,854, 2,095,856, 2,955,939, 3,482,978, 3,552,974, 3,573,921, 3,582,344, 3,623,881 and 3,695,888.

To enhance the sensitivity in the near infra-red region use can be made of so-called supersensitizers in combination with infra-red sensitizing dyes. Suitable supersensitizers are described in Research Disclosure Vol 289, May 1988, item 28952.

The spectral sensitizers can be added to the photosensitive silver halide emulsions in the form of an aqueous solution, a solution in an organic solvent or in the form of a dispersion.

The photosensitive silver halide emulsion and substantially light insensitive silver salt emulsions may contain the usual stabilizers e.g. homopolar or salt-like compounds of mercury with aromatic or heterocyclic rings such as mercaptotriazoles, simple mercury salts, sulphonium mercury double salts and other mercury compounds. Other suitable stabilizers are azaindenes, preferably tetra- or penta-azaindenes, especially those substituted with hydroxy or amino groups. Compounds of this kind have been described by BIRR in Z. Wiss.

Photogr. Photophys. Photochem. 47, 2–27 (1952). Other suitable stabilizers are i.a. heterocyclic mercapto compounds e.g. phenylmercaptotetrazole, quaternary benzothiazole derivatives, and benzotriazole. Preferred compounds are mercapto substituted pyrimidine derivatives as disclosed in U.S. Pat. No. 3,692,527.

The silver halide emulsions may contain pH controlling ingredients. Preferably the emulsion layer is coated at a pH value below the isoelectric point of the gelatin to improve the stability characteristics of the coated layer. Other ingredients such as antifogging agents, development accelerators, wetting agents, and hardening agents for gelatin may be present. The silver halide emulsion layer may comprise light-screening dyes that absorb scattering light and thus promote the image sharpness. Suitable light-absorbing dyes are described in i.a. U.S. Pat. No. 4,092,168, U.S. Pat. No. 4,311,787 and DE-P 2,453,217.

Development acceleration can be accomplished with the aid of various compounds, preferably polyalkylene derivatives having a molecular weight of at least 400 such as those described in e.g. U.S. Pat. Nos. 3,038,805, 4,038,075, 4,292,400.

More details about the composition, preparation and coating of silver halide emulsions can be found in e.g. Product Licensing Index, Vol. 92, December 1971, publication 9232, p. 107–109.

The hydrophilic layers usually contain gelatin as hydrophilic colloid binder. Mixtures of different gelatins with different viscosities can be used to adjust the rheological properties of the layer. Like the emulsion layer to adjust the rheological properties of the layer. Like the emulsion layer the other hydrophilic layers are coated preferably at a pH value below the isoelectric point of the gelatin. But instead of or together with gelatin, use can be made of one or more other natural and/or synthetic hydrophilic colloids, e.g. albumin, casein, zein, polyvinyl alcohol, alginic acids or salts thereof, cellulose derivatives such as carboxymethyl cellulose, modified gelatin, e.g. phthaloyl gelatin etc.

The hydrophilic layers of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethyl hydantoin, dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts of the type, described in U.S. Pat. No. 4,063,952.

In a preferred embodiment of the present invention an intermediate hydrophilic layer, serving as antihalation layer, is provided between the support and the photosensitive silver halide emulsion layer. This layer can contain the same light-absorbing dyes as described above for the emulsion layer; as alternative finely divided carbon black can be used for the same antihalation purposes as described in U.S. Pat. No. 2,327,828. On the other hand, in order to gain sensitivity, imagewise light reflecting pigments, e.g. titaniumdioxide can be present. Further this layer can contain hardening agents, matting agents, e.g. silica particles, and wetting agents. When the photosensitive silver halide and the substantially light insensitive silver salt are present in separate layers the antihalation layer can be provided between both silver salt layers.

The photographic element used according to the present invention may further comprise various kinds of surface-active agents in the photographic emulsion layer or in at least one other hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Preferably compounds containing perfluorinated alkyl groups are used. Such surface-active agents can be used for various purposes e.g. as coating aids, as compounds preventing electric charges, as compounds improving slidability, as compounds facilitating dispersive emulsification and as compounds preventing or reducing adhesion.

The photographic element of the present invention may further comprise various other additives such as e.g. compounds improving the dimensional stability of the photographic element, UV-absorbers, spacing agents or matting agents and plasticizers. Preferred spacing agents are $SiO_2$ particles having an average size of from 0.8 $\mu$m to 15 $\mu$m. These spacing agents may be present in one or more layers comprised on the support of the photographic material.

Suitable additives for improving the dimensional stability of the photographic element are e.g. dispersions of a water-soluble or hardly soluble synthetic polymer e.g. polymers of alkyl (meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, Alpha-Beta-unsaturated dicarboxylic acids, hydroxyalkyl (meth)acrylates, sulphoalkyl (meth)acrylates, and styrene sulphonic acids.

According to the present invention there is provided a method for obtaining an image with the photographic material described above. According to this method the photographic material of the present invention is information-wise exposed and subsequently developed in the presence of developing agents. Suitable developing agents for the exposed silver halide are e.g. hydroquinone-type and 1-phenyl-3-pyrazolidone-type developing agents as well as p-monomethylaminophenol and derivatives thereof. Preferably used is a combination of a hydroquinone-type and 1-phenyl-3-pyrazolidone-type developing agent whereby the latter is preferably incorporated in one of the layers comprised on the support of the photographic material. A preferred class of 1-phenyl-3-pyrazolidone-type developing agents is disclosed in the European patent application number EP-A-449340. It was found that most advantage of the present invention is taken when at least one of the there disclosed developing agents are present in the photographic material of the present invention preferably in the layer(s) comprising the photosensitive and/or substantially light insensitive silver salt particles. Other type of developing agents suitable for use in accordance with the present invention are reductones e.g. ascorbic acid derivatives. Such type of developing agents are disclosed in the European patent application number 91200311.8.

The developing agent or a mixture of developing agents can be present in an alkaline processing solution and/or in the photographic material. In case the developing agent or a mixture of developing agents is contained in the photographic material, the processing solution can be merely an aqueous alkaline solution that initiates and activates the development.

The pH of the alkaline processing solution is preferably between 10 and 13. The desired pH of the processing solution can be reached by incorporating alkaline substances in the processing solution. Suitable alkaline substances are inorganic alkali e.g., sodium hydroxide, potassium carbonate or alkanolamines or mixtures thereof. Preferably used alkanolamines are tertiary alkanolamines e.g. those described in EP-A-397925, EP-A-397926, EP-A-397927, EP-A-398435 and U.S. Pat. No. 4.632.896. A combination of alkanolamines having both a $pk_a$ above or below 9 or a combination of alkanolamines whereof at least one has a $pk_a$ above 9 and another having a $pk_a$ of 9 or less may also be used as disclosed in the Japanese patent applications laid open to the public numbers 73949/61, 73953/61, 169841/61, 212670/60, 73950/61, 73952/61, 102644/61, 226647/63, 229453/63, U.S. Pat. No. 4,362,811, U.S. Pat. No. 4,568,634 etc. The concentration of these alkanolamines is preferably from 0.1 mol/l to 0.9 mol/l.

According to the present invention best results are obtained when the photographic element of the present invention is developed in the presence of a silver halide solvent. Preferably used silver halide solvents are water soluble thiosulphate compounds such as ammonium and sodium thiosulphate, or ammonium and alkali metal thiocyanates. Other useful silver halide solvents (or "complexing agents") are described in the book "The Theory of the Photographic Process" edited by T. H. James, 4th edition, p. 474–475 (1977), in particular sulphites and uracil. Further interesting silver halide complexing agents are cyclic imides, preferably combined with alkanolamines, as described in U.S. Pat. No. 4,297,430 and U.S. Pat. No. 4,355,090. 2-mercaptobenzoic acid derivatives are described as silver halide solvents in U.S. Pat. No. 4,297,429, preferably combined with alkanolamines or with cyclic imides and alkanolamines. Dialkylmethylenedisulfones can also be used as silver halide solvent.

The silver halide solvent is preferably present in the processing solution but may also be present in one or more layers comprised on the support of the photographic element. When the silver halide solvent is incorporated in the photographic material it may be incorporated as a silver halide solvent precursor as disclosed in e.g. Japanese published unexamined patent applications No. 15247/59 and 271345/63, U.S. Pat. No. 4,693,955 and U.S. Pat. No.3,685,991.

The processing solution for use in accordance with the present invention may comprise other additives such as e.g. thickeners, preservatives, detergents e.g. acetylenic detergents such as surfynol 104, surfynol 465, surfynol 440 etc. all available from Air Reduction Chemical Company New York.

The photographic material of the present invention can be used in a variety of application fields e.g. for producing images according to the silver salt diffusion transfer process (hereinafter abbreviated DTR-process), for producing lithographic printing plates according to the DTR-process, for scanning exposure, in Computer Output to Microfilm (COM) applications etc. The use of the photographic material of the present invention in some of these application fields will be described in more detail in the following embodiments.

According to a first application the photographic material of the present invention can be used in a DTR-process to produce negative or positive images. The principles of the silver complex diffusion transfer reversal process have been described e.g. in U.S. Pat. No. 2,352,014 and in the book "Photographic Silver Halide Diffusion Processes" by André Rott and Edith Weyde—The Focal Press—London and New York, (1972).

In the DTR-process non-developed silver halide of an image-wise exposed photographic silver halide emulsion layer material is transformed with a silver halide solvent into soluble silver complex compounds which are allowed to diffuse into an image-receiving layer and are reduced therein with a developing agent, generally in the presence of physical development nuclei, to form a silver image having reversed image density values with respect to the silver image obtained in the exposed photographic material.

The DTR-process was initially intended for office copying purposes but has found now wide application in the graphic art field, more particularly in the production of screened prints from continuous tone originals. For processing DTR-materials according to the present embodiment use can be made of processing solutions described above provided of course that a silver halide solvent of the type described is present in the processing solution and/or in one or more layers of the DTR-material e.g. the image-receiving layer. When the silver halide solvent is incorporated in the photographic material it may be incorporated as a silver halide solvent precursor as disclosed in e.g. Japanese published unexamined patent applications No. 15247/59 and 271345/63, U.S. Pat. No. 4,693,955 and U.S. Pat. No. 3,685,991. When fairly low gradation images for continuous tone reproduction have to be produced preference is given to developing agent combinations as described in U.S. Pat. Nos. 3,985,561 and 4,242,436.

Processing of the DTR-material according to the present invention is preferably carried out using a single processing solution. However the photographic material according to the present embodiment may also be processed using two processing solutions. In the latter case only the second processing liquid used to process contains a silver halide solvent(s).

The alkaline processing solution for use in accordance with this embodiment preferably contains (a) silver image toning agent(s) providing a neutral (black) image tone to the DTR-produced silver image in the image-receiving layer. A survey of suitable toning agents is given in the above mentioned book of André Rott and Edith Weyde, p. 61–65, preference being given to 1-phenyl-5-mercapto-tetrazole, tautomeric structures and derivatives thereof such as 1-(2,3-dimethylphenyl)-5-mercapto-tetrazole, 1-(3,4-dimethylcyclohexyl)-5-mercapto-tetrazole,
1-(4-methyl phenyl)-5-mercapto-tetrazole,
1-(3-chloro-4-methylphenyl)-5-mercapto-tetrazole,
1-(3,4-dichlorophenyl)-5-mercapto-tetrazole.

Other suitable black toning agents for use in accordance with the present embodiment are those disclosed in the European patent applications 218752, 208346, 218753 and U.S. Pat. No. 4683189.

For DTR-processing the aqueous alkaline processing solution may comprise (a) toning agent(s) in a concentration in a range e.g. from 30 mg to 200 mg per liter. Said toning agents may also at least partially be present in the image receiving layer and/or in a layer in water permeable relationship therewith.

Other additives for the processing solution are thickening agents, e.g. hydroxyethylcellulose and carboxymethylcellulose, fog inhibiting agents, e.g. potassium bromide, potassium iodide and a benzotriazole, calcium-sequestering compounds, wetting agents, e.g. block copolymers of ethyleneoxide or of propylene oxide, anti-sludge agents, and hardeners including latent hardeners.

The DTR-image can be formed in the image-receiving layer of a sheet or web material being a separate element with respect to the photographic silver halide emulsion material or in a so-called single-support-element, also called mono-sheet element or unitary DTR-material, which contains at least one photographic silver halide emulsion layer and the image-receiving layer in water permeable relationship therewith, e.g. on top of each other or separated by a thin water permeable stripping layer or alkali-degradable interlayer as described e.g. in U.S. Pat. No. 3,684,508 or wherein the photographic silver halide emulsion layer is optically masked from the image-receiving layer, e.g. with a white water permeable pigment layer as described e.g. in U.S. Pat. No. 3,607,270 and 3,740,220.

When the DTR-image is formed on a separate sheet called image receiving material the information-wise exposed photographic material is processed in the processing liquid while in contact with said receiving material. Alternatively the processing liquid may be applied to either the image-receiving material or photographic material before contacting both elements. Both elements are usually kept in contact with each other for 30s to 1 min.

The support of the image receiving material and/or photographic material may be opaque or transparent, e.g. a paper support or resin support. The image receiving layer comprises for best imaging results physical development nuclei normally in the presence of a protective hydrophilic colloid, e.g. gelatin, polyvinyl alcohol, polyvinyl pyrrolidone, poly(meth)acryl amide etc. or mixtures thereof, and/or colloidal silica.

Preferred development nuclei are sulphides of heavy metals e.g. sulphides of antimony, bismuth, cadmium, cobalt, lead, nickel, palladium, platinum, silver, and zinc. Especially suitable development nuclei are NiS-.Ag₂S nuclei as described in U.S. Pat. No. 4,563,410. Other suitable development nuclei are salts such as e.g., selenides, polyselenides, polysulphides, mercaptans, and tin (II) halides. Heavy metals or salts thereof and fogged silver halide are suitable as well. The complex salts of lead and zinc sulphides are active both alone and when mixed with thioacetamide, dithiobiuret, and dithiooxamide. Heavy metals, preferably silver, gold, platinum, palladium, and mercury can be used in colloidal form.

According to a preferred mode of the present embodiment in the image-receiving element the development nuclei containing layer and/or hydrophilic colloid layer in water permeable relationship or a back layer at the side of the support opposite to that carrying the image receiving layer contains at least part of the silver image toning agents. Such procedure results actually in automatic replenishment of toning agent in the processing liquid. The same applies at least partly for the replenishment of the developing agent(s) and silver halide complexing agent(s).

At least a part of said silver image toning agents may be present in the silver halide emulsion material to be developed. This means that in a practical embodiment at least one of the image toning agents may be used in a hydrophilic water permeable colloid layer, e.g. antihalation layer at the side of the support opposite to the side coated with the photosensitive silver halide emulsion layer or between the support and the silver halide emulsion layer. The coverage of said silver image toning agents in said antihalation layer is preferably in the range of 1 mg/m² to 20 mg/m².

Said layer at the side of the support opposite to the side coated with the photosensitive silver halide emulsion layer may also contain anti-sludge agents for reducing the contamination of the processing liquid. Suitable anti-sludge agents are disclosed in e.g. EP-223883, U.S. Pat. No. 3438777, BE-P-606550 and GB-P-1120963. Further anti-sludge agents suitable for use in accordance with the present invention correspond to the following general formula:

Q—SH wherein Q represents an alkyl or alkylaryl group containing at least 7 carbons in a straight line.

The transfer behaviour of the complexed silver largely depends on the thickness of the image-receiving layer and the kind of binding agent or mixture of binding agents used in the nuclei containing layer. In order to obtain a sharp image with high spectral density the reduction of the silver salts diffusing into the image receiving layer must take place rapidly before lateral diffusion becomes substantial. An image-receiving material satisfying said purpose is described in U.S. Pat. No. 4,859,566.

A white appearance of the image background even when a yellow stain would appear on storage is obtained by incorporation of optical brightening agents in the support, image-receiving layer and/or interlayer between the support and the image-receiving layer.

In the image-receiving layer and/or in an undercoat gelatin is used preferably as hydrophilic colloid. In these layer(s) gelatin is present preferably for at least 60% by weight and is optionally used in conjunction with an other hydrophilic colloid, e.g. polyvinyl alcohol, cellulose derivatives, preferably carboxymethyl cellulose, dextran, gallactomannans, alginic acid derivatives, e.g. alginic acid sodium salt and/or water soluble polyacrylamides.

The image-receiving layer or a hydrophilic colloid layer in water-permeable relationship therewith may comprise colloidal silica.

The image-receiving layer may contain as physical development accelerators, in operative contact with the developing nuclei, thioether compounds such as those described e.g. in DE-A-1,124,354; U.S. Pat. No. 4,013,471; U.S. Pat. No. 4,072,526; and in EP 26520.

When applying an optical brightening agent in the image-receiving material preference is given to an optical brightening agent that is inherently by its structure resistant to diffusion or is made resistant to diffusion by use in conjunction with another substance wherein it is dissolved or whereto it is adsorbed.

The image-receiving layer and/or other hydrophilic colloid layer of an image-receiving material used in a DTR-process according to the present embodiment may have been hardened to some extent to achieve enhanced mechanical strength. Appropriate hardening agents for hardening the natural and/or synthetic hydrophilic colloid binding agents in the image-receiving layer include e.g. formaldehyde, glyoxal, mucochloric acid, and chrome alum. Other suitable hardening agents for hardening the hydrophilic colloid binding agents in the image-receiving layer are vinylsulphonyl hardeners, e.g. as described in Research Disclosure 22,507 of January 1983.

According to a second application the photographic material can be used for manufacturing a lithographic printing plate precursor and for manufacturing a printing plate using the DTR-process. A DTR-image bearing material can be used as a planographic printing plate wherein the DTR-silver image areas form the water-repellant ink-receptive areas on a water-receptive ink-repellant surface. The DTR-image can be formed in the image-receiving layer of a sheet or web material having a hydrophilic surface which is a separate element with respect to the photographic silver halide emulsion material (a so-called two-sheet DTR element) disclosed in e.g. DE-A-2,346,378 or in the image-receiving layer of a so-called single-support-element, also called mono-sheet element, which contains at least one photographic silver halide emulsion layer integral with an image-receiving layer in water permeable relationship therewith. It is the latter mono-sheet version which is preferred for the preparation of offset printing plates by the DTR method.

Todate on the market lithographic printing plates made according to the DTR-process are positive working lithographic printing plates i.e. the non-exposed areas of a negative working silver halide will correspond to the printing areas on the plate. Most originals used for making a lithographic printing plate require reversal of the image which would not be required with a negative working printing plate. Furthermore, since only the image-areas have to be exposed on a negative working lithographic printing plate time can be saved in the imaging of such a printing plate with a laser. As described above the present invention offers the possibility to obtain a negative working lithographic printing plate without loss of speed.

According to the method of the present invention for making a lithographic printing plate an imaging element containing a photosensitive silver halide and substantially light insensitive silver halide having a speed at least a factor 10 less than said photosensitive silver halide and a releasing compound capable of releasing a sulphide is information-wise exposed and developed in the presence of (a) developing agent (s) and (a) silver halide solvent(s) while in contact with an image receiving layer that may be contained on a separate support, a so-called two-sheet DTR-material or may be contained in the imaging element a so called monosheet DTR-material. Subsequent thereto the developed printing plate is preferably treated with a neutralization solution containing buffer substances to neutralize the alkaline plate after treatment with the developing liquid.

Normally in lithographic printing greasy inks are employed. So, to obtain good prints it is necessary that the difference in oleophilic and hydrophilic (oleophobic) properties of the image and background surface is sufficiently distinct so that when water and ink are applied during the printing process, the image will accept sufficient ink leaving the background clean.

Suitable methods to enhance the differentiation in ink acceptance between the hydrophobic silver image parts and the hydrophilic non-image parts for use in connection with the present invention are as follows. Use can be made of so-called hydrophobizing agents to improve the ink acceptance of the silver image parts and which can be present, depending on the case, in one of the normal processing solutions of the DTR process, or in a separate solution, a so-called lithographic fixer. For example, U.S. Pat. No. 3,776,728 describes i.a. developer solutions which contain a heterocyclic mercapto-compound, e.g. a 2-mercapto-1,3,4-oxadiazole derivative, as hydrophobizing agent. U.S. Pat. No. 4,563,410 describes hydrophobizing liquids containing one or more mercaptotriazole or mercaptotetrazole derivatives or mixtures thereof.

Another method of enhancing the hydrophobic character of the silver image that can be used in accordance with the present invention consists in maximizing the ratio of the amount of development nuclei to the amount of hydrophilic binder, e.g. gelatin, in the development nuclei containing surface layer where the DTR-image is formed. For example U.S. Pat. No. 3,728,114 describes a direct positive sheet suitable for producing an offset printing plate which contains in its surface layer at most 30% of a high molecular weight compound, e.g. gelatin, relative to the weight of the nuclei.

Two types of mono-sheet DTR lithographic printing plate precursors are known and can be used in accordance with the present invention. A first type of lithographic printing plate precursor comprises a hydrophilic support e.g. an anodized aluminium support provided with an image-receiving layer and a photosensitive silver halide emulsion, substantially light insensitive silver salt particles and a sulphide releasing compound. This lithographic printing plate precursor is then imagewise exposed and developed according to the DTR-process. After said development the layers above the image-receiving layer are removed by rinsing with water so that the silver image formed in the image-receiving layer is exposed and can be used to print.

The second type of lithographic printing plate precursor comprises on a support a photosensitive silver halide emulsion layer, substantially light insensitive silver salts, a sulphide releasing compound and an image receiving layer as the outermost layer. According to the method for obtaining a lithographic printing plate with this type of precursor said precursor is information-wise exposed and development according to DTR-process and the imaged lithographic printing plate precursor is used to print without separation of the now useless silver halide emulsion layer.

The image-receiving layer for use in accordance with the present embodiment is preferably a layer of physical development nuclei and which layer is preferably substantially free of binding agents. Physical development nuclei suitable for use in accordance with this embodiment are the physical development nuclei described above. Preferably used physical development nuclei are heavy metal sulphides e.g. palladium sulphide.

Suitable supports for the lithographic printing plate precursor are metal supports preferably aluminium or zinc, paper supports preferably polyethylene coated paper supports disclosed in e.g. Japanese patent no. 1.030.140, polyester film supports preferably polyethylene terephthalate.

Metal supports are especially suitable for lithographic printing plates according to the first type. For example an anodized aluminium foil can be provided with a layer containing physical development nuclei directly to the support. To this layer is then preferably applied a layer containing a non-proteinic hydrophilic film forming polymer, latex particles or mixtures thereof as disclosed in EP-A-483415 and EP-A-410500. To the thus obtained element a layer containing the photosensitive silver halide particles, the substantially light insensitive silver salt particles and the releasing compound is finally applied. According to a variation the photosensitive silver halide particles and the substantially light insensitive silver salt particles can be present in separate layers the releasing compound then being present in one or both of these layers. The arrangement of these separate layers being preferably so that the layer containing the photosensitive silver halide particles is the remotest from the support. The releasing compound may also be present in other layers comprised on the photosensitive side of the support.

When a paper support or polyester film support is used the layer arrangement described above is reversed so that the physical development nuclei layer is the remotest from the support. A lithographic printing plate precursor of the second type described above is thus obtained.

In the past several developments that can be used in accordance with the present invention have taken place for improving the storage stability, printing properties, photographic properties etc. of these printing plates and/or printing plate precursors of the second type. In accordance with the present invention it is advantageous with respect to storage stability to include developing agents of the hydroquinone type and of the 1-phenyl-3pyrazolidone type in the photographic material in a ratio by weight of the hydroquinone type to the 1-phenyl-pyrazolidone type not more than 2.5 and preferably between 2.0 and 0.8.

Preferably the lithographic printing plate precursor also includes so called matting agent in a hydrophilic base layer comprised between the support and the subsequent layers comprised on the support. The matting agent may also be included in other layer such as the layer(s) containing the photosensitive and/or substantially light insensitive silver salt particles but preferably at least 80% of the total amount is included in the base layer. Suitable matting agent for use in accordance with the present embodiment are organic or inorganic particles having an average size of 0.8 $\mu$m to 20 $\mu$m preferably between 2 $\mu$m and 10 $\mu$m. Mixtures of matting agents having different sizes may also be used. Examples of inorganic particles are $SiO_2$, $TiO_2$, $Al_2O_3$, clay etc. Examples of organic particles are latex particles of homopolymers and/or copolymers of (meth)acrylate.

With respect to the printing endurance it is further advantageous to include a hydrophilic colloid layer contiguous to the image-receiving layer. Especially good results are obtained when said hydrophilic colloid layer is used in accordance with the present invention.

Said hydrophilic colloid layer is preferably gelatin. To increase the printing endurance a benztriazole may be included in the lithographic printing plate precursor and/or the processing solution as disclosed in e.g. U.S. Pat. No. 4,824,760.

According to a third application of the present invention the photographic material can be used for preparing a positive working silver halide photographic material having a high speed. Such type of materials are commonly employed in COM-applications as well as in the graphic arts field. Todate positive working materials for use in COM-applications are based on direct positive silver halide emulsions. These type of silver halide emulsions are however less sensitive than negative silver halide emulsions.

Since it is possible according to the present invention to obtain a positive working photographic material with a negative photosensitive silver halide emulsion a high speed positive working photographic material can be obtained. For this purpose a support e.g. a paper or resin support is provided with a layer comprising a negative working photosensitive silver halide emulsion, substantially light insensitive silver salt particles and a sulphide releasing compound according to the invention that is capable of releasing sulphide mainly in the non-exposed areas. During development the sulphide will be released in the non-exposed areas where it renders the the substantially light insensitive and possibly the photosensitive silver salt developable. However in the exposed areas the photosensitive silver halide will also develop thus yielding a certain density in the exposed areas which is not desired. To decrease the density in the exposed areas the amount of photosensitive silver halide is kept as low as possible preferably below 0.5 g of $AgNO_3/m^2$ and the average grain size (diameter) is preferably more than 0.4 $\mu$m. To further reduce the density in the exposed areas use can be made of compounds that release a development inhibitor in the exposed areas upon development. For example development inhibitor releasing compounds disclosed in e.g. EP-A-347849, the U.S. Pat. Nos. 3,148,062, 3,227,554, 3,733,201, 3,617,291, 3,980,479, 3,933,500, 4,248,962, 4,409,323 and 4,684,604 can be used.

Said development step is preferably followed by a washing step, a fixing step and another washing or stabilizing step. The first washing step may be omitted.

According to a variation of the present embodiment the photosensitive and substantially light insensitive silver salt particles are present in separate layers the preferred mode however being the above described mode.

According to a fourth application of the present invention a negative working photographic material may be prepared in a similar way as described in the third application with the difference however that a releasing compound is comprised in the photographic material that releases sulphide during development mainly in the exposed areas of a negative working photosensitive silver halide.

The present invention will now be illustrated with the following examples without limiting the present invention thereto. All parts are by weight unless otherwise specified.

EXAMPLE 1

Preparation of the substantially light insensitive silver halide emulsion.

| Solution A (40° C.): | water | 1000 ml |
| | AgNO₃ | 332 g |
| Solution B (40° C.): | water | 100 ml |
| | NaCl | 42.3 g |
| Solution C (40° C.): | water | 900 ml |
| | KBr | 5.6 g |
| | NaCl | 377 g |
| Solution D (40° C.): | gelatin | 50 g |

Solution D was brought to pH 4.0 with a sulfuric acid solution and to a pAg of 105 mV with a sodium chloride solution. Subsequently solution A was added at a constant rate, while solution B was added at a rate so as to keep the pAg at 105 mV. Solution A was further added at an accelerating rate, while solution C was added at a rate sufficient to keep the pAg constant. The resulting silver halide emulsion was precipitated by adding polystyrene sulphonic acid. The precipitate was rinsed several times and redispersed by adding 180 g of gelatin per 2.2 kg of precipitate. A substantially light insensitive silver halide emulsion containing 99 mol % of silver chloride and 1mol % of silver bromide was thus obtained. The average grain size was 0. 155 μm.

Preparation of the photosensitive silver halide emulsion.

| Solution E (20° C.): | AgNO₃ | 1.7 g |
| | water | 1000 ml |
| Solution F (20° C.): | water | 250 ml |
| | NaCl | 11,3 g |
| Solution G (40° C.): | water | 995 ml |
| | AgNO₃ | 33 g |
| Solution H (40° C.): | water | 1250 ml |
| | NaCl | 668 g |
| | KBr | 4,4 g |
| | H₂SO₄ (1N) | 47.5 ml |
| Solution I (58° C.): | NaCl | 5.66 g |
| | gelatin | 90 g |
| | H₂SO₄ (1N) | 24 ml |
| | water | 2500 ml |

Solution E and F were simultaneously added to solution I in 3 min., After 10 min. 42 μg rhodium(III)hexachloride was added, Solution G was then added to solution I in 5 min. and subsequently solution H was added to solution I in 8 min. Physical ripening was carried out for 40 min. at 65° C., whereafter 0.6 ml of a potassium iodide solution (3 mol/1) were added. The silver halide emulsion was subsequently ripened with gold and thiosulphate and precipitated with polystyrene sulphonic acid. After washing the silver halide emulsion was stabilized with triazaindolizine and redispersed with 160 g of gelatin per 566 kg of silver expressed as AgNO₃. The silver halide emulsion was then spectrally sensitized with an ortho sensitizer. A silver halide emulsion with a composition of 98.5% AgCl, 1.3% AgBr and 0.2% AgI was obtained with an average grain size of 0.41 μm.

Preparation of a lithographic printing plate precursor.

To a polyethylene terephthalate film support coated with a hydrophilic adhesion layer was coated a layer containing a mixture of the above described photosensitive silver halide emulsion and the above described substantially light insensitive silver halide emulsion in a total amount of silver halide corresponding to 2.8 g AgNO3/m². 18% of the total amount of AgNO₃ in the layer corresponded to the photosensitive silver halide. This layer further contained 0.446 mmol/m² of hydroquinone, 0.34 mmol/m² of a 1-phenyl-3-pyrazolidone and a dispersion of compound 1 mentioned in the description in an amount of 0.467 mmol/m² To the thus obtained element was then applied a finishing layer of gelatin in an amount of 0.6 g gelatin per m² and a layer of PdS physical development nuclei.

Preparation of the lithographic printing plate.

The thus obtained lithographic printing plate precursor was image-wise exposed through a negative original for 1.3s with a halogen light source and subsequently processed as follows:

| 15s in an activator solution with the following composition: | |
|---|---|
| cyclohexanedimethylol | 25 g/l |
| methylpropylpropaandiol | 25 g/l |
| Na₂CO₃ | 14 g/l |
| NaOH | 70,9 g/l |
| 30s in a transfer developer with the following composition: | |
| NaOH | 30 g/l |
| hydroquinone | 13 g/l |
| 1-phenyl-4,4-dimethyl-3-pyrazolidone | 5 g/l |
| KSCN | 7 g/l |
| 5-heptyl-2-mercapto-1,3,4-oxadiazole | 0.5 g/l |
| 30s in a stabilising liquid with the following composition: | |
| NaH₂PO₄.2H₂O | 60 g/l |
| Na₂HPO₄.12H₂O | 10 g/l |
| Na₂SO₃ | 5 g/l |
| Cysteine.HCl.H₂O | 1 g/l |
| Ammoniumperfluorocaprylate | 0.2 g/l |

The thus obtained negative working printing plate was installed on an ABDIck 360 printing press. Up to 1000 copies of good quality were printed using a greasy ink (K+E123W ink obtained from Kast & Ehinger) and a conventional fountain solution.

We claim:

1. A photographic material comprising on a support photosensitive silver halide particles, and substantially light insensitive silver salt particles having a speed at least a factor 10 less under the same conditions of exposure and development of said photosensitive silver halide particles than said photosensitive silver halide particles and a releasing compound of formula (I) or (II) capable of image-wise releasing a sulphide or sulphide under conditions for image-wise development of said photosensitive silver halide particles to silver:

$$\text{CARRIER}-(\text{TIME})_n-\text{S}-\text{A} \qquad (I)$$

$$(II)$$

CARRIERS wherein CARRIER represents a carrier moiety that upon reaction with either the reduced or oxidized form of a developing agent or upon reaction with silver ions is capable of releasing under the conditions of development of said photosensitive silver halide the moiety -(TIME)$_n$-S-A, -S-A or sulphide, TIME represents a timing group which releases -S-A or sulphide subsequent to the release of -(TIME)$_n$-S-A from CARRIER, A represents an organic group that renders the bond between S and A readily splittable under the development conditions of said photosensitive silver halide and n represents 0 or 1.

2. A photographic material according to claim 1 wherein said substantially light insensitive silver salt particles are silver halide particles.

3. A photographic material according to claim 1 wherein said releasing compound corresponds to one of the following formulas (III) to (VI):

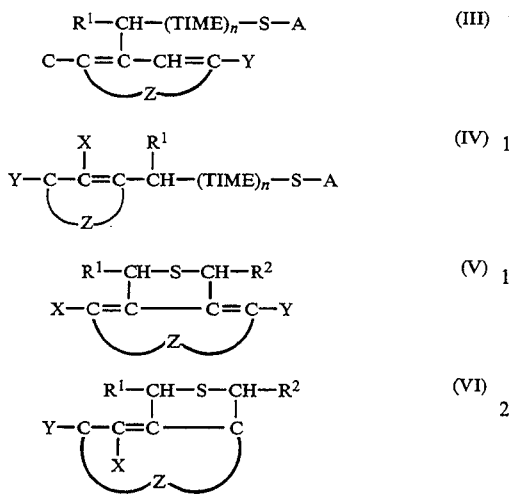

wherein $R^1$, $R^2$ each independently represents hydrogen or an alkyl containing 1 to 5 carbon atoms;

Z represents the necessary atoms for completing an aromatic ring and that may be substituted with one or more substituents;

X represents —$OR^3$ with $R^3$ hydrogen or a hydrolizable group yielding hydroxy, —$NHR^4$ with $R^4$ an alkyl, aryl, aralkyl each of which may be substituted, —N=O or —$NO_2$;

Y represents independently from X represents one of the significances given for X or —$NHSO_2$—$R^4$; and A, TIME and n are as defined in claim 1.

4. A photographic material according to claim 1 wherein A is hydrogen, an acyl, para-hydroxy benzyl, ortho-hydroxy benzyl each of which may be substituted, —$CH_2$—NHCOR, —$CH_2$—O—COR with R a hydrogen, alkyl, aryl or aralkyl each of which may be substituted.

5. A photographic material according to claim 1 wherein said photosensitive silver halide particles and said substantially light insensitive silver salt particles are present in the same layer.

6. A photographic material according to claim 1 further comprising a silver halide solvent or silver halide solvent precursor.

7. A photographic material according to claim 6 wherein said silver halide solvent is a cyclic imide, a 2-mercaptobenzoic acid, an alkanolamine or a mixture thereof.

8. A photographic material according to claim 1 additionally comprising a layer of physical development nuclei.

9. A method for obtaining an image comprising the steps of:
information-wise exposing a photographic material comprising on a support photosensitive silver halide particles, and substantially light insensitive silver salt particles having a speed at least a factor 10 less under the same conditions of exposure and development of said photosensitive silver halide particles than said photosensitive silver halide particles and a releasing compound of formula (I) or (II) capable of image-wise releasing a sulphide or sulphide under conditions for image-wise development of said photosensitive silver halide particles to silver:

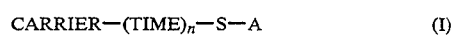

(I)

(II)

CARRIERS wherein CARRIER represents a carrier moiety that upon reaction with either the reduced or oxidized form of a developing agent or upon reaction with silver ions is capable of releasing under the conditions of development of said photosensitive silver halide the moiety -(TIME)$_n$-S-A, -S-A or sulphide, TIME represents a timing group which releases -S-A or sulphide subsequent to the release of -(TIME)$_n$-S-A from CARRIER, A represents an organic group that renders the bond between S and A readily splittable under the development conditions of said photosensitive silver halide and n represents 0 or 1, developing said information-wise exposed photographic material in an alkaline processing solution in the presence of (a) developing agent(s).

10. A method according to claim 9 wherein said substantially light insensitive silver salt particles are silver halide particles.

11. A method according to claim 9, wherein said releasing compound corresponds to one of the following formulas (III) to (VI):

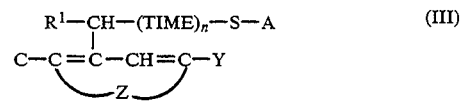

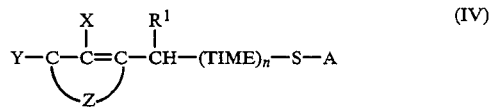

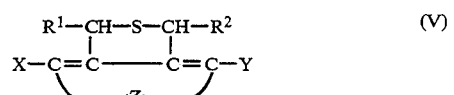

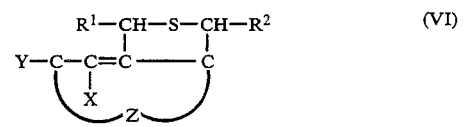

wherein $R^1$ $R^2$ each independently represents hydrogen or an alkyl containing 1 to 5 carbon atoms;

Z represents the necessary atoms for completing an aromatic ring and that may be substituted with one or more substituents;

X represents —$OR^3$ with $R^3$ hydrogen or a hydrolizable group yielding hydroxy, —$NHR^4$ with $R^4$ an alkyl, aryl, aralkyl each of which may be substituted, —N=O or —$NO_2$;

Y represents independently from X represents one of the significances given for X or —$NHSO_2$—$R^4$; and A, TIME and n are as defined in claim 9.

12. A method according to claim 9 wherein said developing is carried out in the presence of a silver halide solvent.

13. A method according to claim 12 wherein said silver halide solvent is a thiocyanate, a thiosulphate, a cyclic imide, a 2-mercaptobenzoic acid, an alkanolamine or a mixture thereof.

14. A method for obtaining an image according to the DTR-process comprising the steps of:

information-wise exposing a photographic material comprising on a support photosensitive silver halide particles, and substantially light insensitive silver salt particles having a speed at least a factor 10 less under the same conditions of exposure and development of said photosensitive silver halide particles than said photosensitive silver halide particles and a releasing compound of formula (I) or (II) capable of image-wise releasing a sulphide or sulphide under conditions for image-wise development of said photosensitive silver halide particles to silver:

$$\text{CARRIER}-(\text{TIME})_n-\text{S}-\text{A} \quad (I)$$

$$(II)$$

CARRIERS

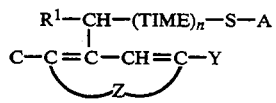

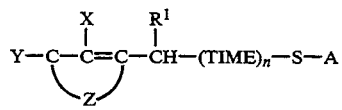

wherein CARRIER represents a carrier moiety that upon reaction with either the reduced or oxidized form of a developing agent or upon reaction with silver ions is capable of releasing under the conditions of development of said photosensitive silver halide the moiety -(TIME)$_n$-S-A, -S-A or sulphide, TIME represents a timing group which releases -S-A or sulphide subsequent to the release of -(TIME)$_n$-S-A from CARRIER, A represents an organic group that renders the bond between S and A readily splittable under the development conditions of said photosensitive silver halide and n represents 0 or 1, contacting said information-wise exposed photographic material with an image-receiving material comprising on a support a layer containing physical development nuclei, developing said information-wise exposed photographic material whilst in contact with said image-receiving material in an alkaline processing solution in the presence of (a) developing agent(s) and (a) silver halide solvent(s), separating said image-receiving material from said photographic material.

15. A method according to claim 14 wherein said substantially light insensitive silver salt particles are silver halide particles.

16. A method according to claim 14 wherein said releasing compound corresponds to one of the following formulas (III) to (VI):

$$\text{R}^1-\text{CH}-(\text{TIME})_n-\text{S}-\text{A} \quad (III)$$

C—C=C—CH=C—Y (with Z bridge)

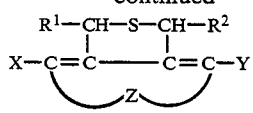

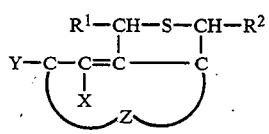

wherein R$^1$, R$^2$ each independently represents hydrogen or an alkyl containing 1 to 5 carbon atoms;

Z represents the necessary atoms for completing an aromatic ring and that may be substituted with one or more substituents;

X represents —OR$^3$ with R$^3$ hydrogen or a hydrolizable group yielding hydroxy, —NHR$^4$ with R$^4$ an alkyl, aryl, aralkyl each of which may be substituted, —N=O or —NO$_2$;

Y represents independently from X represents one of the significances given for X or —NHSO$_2$—R$^4$;

and A, TIME and n are as defined in claim 14.

17. A method for obtaining an image according to the DTR-process comprising the steps of:

information-wise exposing a photographic material comprising on a support (i) photosensitive silver halide particles, (ii) substantially light insensitive silver salt particles having a speed at least a factor 10 less under the same conditions of exposure and development of said photosensitive silver halide particles than said photosensitive silver halide particles, (iii) an image receiving layer containing physical development nuclei and (iv) a releasing compound of formula (I) or (II) capable of image-wise releasing a sulphide or sulphide under conditions for image-wise development of said photosensitive silver halide particles to silver:

$$\text{CARRIER}-(\text{TIME})_n-\text{S}-\text{A} \quad (I)$$

$$(II)$$

CARRIERS wherein CARRIER represents a carrier moiety that upon reaction with either the reduced or oxidized form of a developing agent or upon reaction with silver ions is capable of releasing under the conditions of development of said photosensitive silver halide the moiety -(TIME)$_n$-S-A, -S-A or sulphide, TIME represents a timing group which releases -S-A or sulphide subsequent to the release of -(TIME)$_n$-S-A from CARRIER, A represents an organic group that renders the bond between S and A readily splittable under the development conditions of said photosensitive silver halide and n represents 0 or 1, and developing said information-wise exposed photographic material in an alkaline processing solution in the presence of (a) developing agent(s) and (a) silver halide solvent(s).

18. A method for preparing a lithographic printing plate according to the DTR-process comprising the steps of:

information-wise exposing a photographic material comprising on a support photosensitive silver halide particles, and substantially light insensitive silver salt particles having a speed at least a factor 10 less under the same conditions of exposure and development of said photosensitive silver halide particles than said photosensitive silver halide particles and a releasing compound of formula (I) or (II) capable of image-wise releasing a sulphide or sulphide under conditions for image-wise development of said photosensitive silver halide particles to silver:

CARRIER—(TIME)$_n$—S—A  (I)

CARRIERS  (II)

wherein CARRIER represents a carrier moiety that upon reaction with either the reduced or oxidized form of a developing agent or upon reaction with silver ions is capable of releasing under the conditions of development of said photosensitive silver halide the moiety -(TIME)$_n$-S-A, -S-A or sulphide, TIME represents a timing group which releases -S-A or sulphide subsequent to the release of -(TIME)$_n$-S-A from CARRIER, A represents an organic group that renders the bond between S and A readily splittable under the development conditions of said photosensitive silver halide and n represents 0 or 1, contacting said information-wise exposed photographic material with an image-receiving material comprising on a support a layer containing physical development nuclei and having a hydrophilic surface, developing said information-wise exposed photographic material whilst in contact with said image-receiving material in an alkaline processing solution in the presence of (a) developing agent(s) and (a) silver halide solvent(s), separating said image-receiving material from said photographic material.

19. A method according to claim 18 wherein said substantially light insensitive silver salt particles are silver halide particles.

20. A method according to claim 18 wherein said releasing compound corresponds to one of the following formulas (III) to (VI):

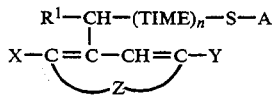  (III)

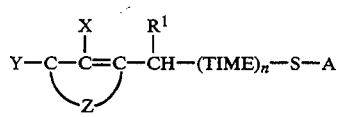  (IV)

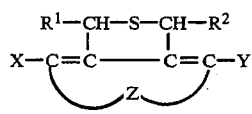  (V)

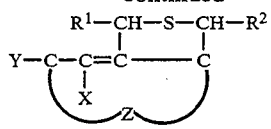  (VI)

wherein R$^1$, R$^2$ each independently represents hydrogen or an alkyl containing 1 to 5 carbon atoms;

Z represents the necessary atoms for completing an aromatic ring and that may be substituted with one or more substituents;

X represents —OR$^3$ with R$^3$ hydrogen or a hydrolizable group yielding hydroxy, —NHR$^4$ with R$^4$ an alkyl, aryl, aralkyl each of which may be substituted, —N=O or —NO$_2$;

Y represents independently from X represents one of the significances given for X or —NHSO$_2$—R$^4$;

and A, TIME and n are as defined in claim 18.

21. A method for preparing a lithographic printing plate according to the DTR-process comprising the steps of:

information-wise exposing a lithographic printing plate precursor comprising on a support (i) a photosensitive silver halide, (ii) a substantially light insensitive silver salt having a speed at least a factor 10 less than said photosensitive silver halide particles under the same conditions of exposure and development of said photosensitive silver halide particles and (iii) a releasing compound as defined in any of claims 1, 3 or 4 capable of image-wise releasing under the conditions for image-wise development of said photosensitive silver halide to silver a sulphide and (iv) a layer of physical development nuclei as an outermost layer on the photosensitive side of said support, and developing said information-wise exposed photographic material in an alkaline processing solution in the presence of (a) developing agent(s) and (a) silver halide solvent(s).

22. A method for preparing a lithographic printing plate according to claim 21 wherein the support of said photographic material is paper or a polyester film support.

23. A method for preparing a lithographic printing plate according to the DTR-process comprising the steps of:

information-wise exposing a lithographic printing plate precursor comprising on a hydrophilic support provided with an image receiving surface or image receiving layer containing physical developement nuclei (i) a photosensitive silver halide, (ii) a substantially light insensitive silver salt having a speed at least a factor 10 less than said photosensitive silver halide particles under the same conditions of exposure and development of said photosensitive silver halide particles and (iii) a releasing compound as defined in any of claims 1, 3 or 4 capable of image-wise releasing under the conditions for image-wise development of said photosensitive silver halide to silver sulphide, developing said information-wise exposed photographic material in an alkaline processing solution in the presence of (a) developing agent(s) and (a) silver halide solvent(s) to obtain a silver image on said image receiving surface or in said image receiving layer, and removing all layers above said silver image to expose said silver image by means of rinsing with water.

24. A method according to claim 23 wherein said hydrophilic support is an aluminium support.

25. A photographic material according to claim 3 wherein said aromatic ring is a benzene ring.

26. A photographic material according to claim 3 wherein said aromatic ring is a naphthalene ring.

27. A photographic material according to claim 11 wherein said aromatic ring is a benzene ring.

28. A photographic material according to claim 11 wherein said aromatic ring is a naphthalene ring.

29. A photographic material according to claim 16 wherein said aromatic ring is a benzene ring.

30. A photographic material according to claim 16 wherein said aromatic ring is a naphthalene ring.

31. A photographic material according to claim 20 wherein said aromatic ring is a benzene ring.

32. A photographic material according to claim 20 wherein said aromatic ring is a naphthalene ring.

* * * * *

UNITED STATES PATENT AND TRADEMARK OFFICE
CERTIFICATE OF CORRECTION

PATENT NO. : 5,348,836
DATED : September 20, 1994
INVENTOR(S) : Ludo Van Rompuy et al It is certified that error appears in the above-indentified patent and that said Letters Patent is hereby corrected as shown below:

Column 1, line 64 "CARRIERS" should read -- CARRIER(S --;

Column 4, formula (III), line 19, "C-C=C-CH=C-Y" should read -- X-C=C-CH=C-Y --;

Column 4, lines 44 and 45, "aralkyl alkoxy" should read -- aralkyl, alkoxy --;

Column 9, lines 56 and 57, "2 g of AgNO/m$_3$/m$^2$" should read -- 2g of AgNO$_3$/m$^2$ --;

Column 11, line 50, "2,3-dihydroxy -dioxan," should read -- 2,3-dihydroxy-dioxan, --;

Column 19, lines 43 and 44, "1-phenyl-3pyrazolidone type" should read -- 1-phenyl-3-pyrazolidone type --;

Column 21, lines 41 and 42, "solution I in 3 min.," should read -- solution I in 3 min.. --;

Column 21, line 43, "chloride was added," should read -- chloride was added. --;

UNITED STATES PATENT AND TRADEMARK OFFICE
CERTIFICATE OF CORRECTION

PATENT NO. : 5,348,836
DATED : September 20, 1994
INVENTOR(S) : Ludo Van Rompuy et al It is certified that error appears in the above-indentified patent and that said Letters Patent is hereby corrected as shown below:

Column 22, claim 1, line 51, "CARRIERS" should read -- CARRIER(S --;

Column 23, claim 3, formula (III), line 7, "C-C=C-CH=C-Y" should read -- X-C=C-CH=C-Y --;

Column 24, claim 9, line 8, "CARRIERS" should read -- CARRIER(S --;

Column 24, claim 11, formula (III), line 36, "C-C=C-CH=C-Y" should read -- X-C=C-CH=C-Y --;

Column 24, claim 11, line 54, "wherein $R^1R^2$ each" should read -- wherein $R^1$, $R^2$ each --;

Column 25, claim 14, line 24, "CARRIERS" should read -- CARRIER(S --;

Column 25, claim 16, formula (III), line 61, "C-C=C-CH=C-Y" should read -- X-C=C-CH=C-Y --;

UNITED STATES PATENT AND TRADEMARK OFFICE
CERTIFICATE OF CORRECTION

PATENT NO. : 5,348,836
DATED : September 20, 1994
INVENTOR(S) : Ludo Van Rompuy et al It is certified that error appears in the above-indentified patent and that said Letters Patent is hereby corrected as shown below:

Column 26, claim 17, line 45, "CARRIERS" should read
-- CARRIER'S --;

Column 27, claim 18, line 18, "CARRIERS" should read
-- CARRIER'S --;

Signed and Sealed this

Twenty-eighth Day of May, 1996

Attest:

BRUCE LEHMAN

*Attesting Officer*　　　　*Commissioner of Patents and Trademarks*